United States Patent [19]

McInerney

[11] Patent Number: 5,105,452

[45] Date of Patent: Apr. 14, 1992

[54] DEVICE FOR DETERMINING THE CHARACTERISTICS OF BLOOD FLOW THROUGH CORONARY BYPASS GRAFTS

[76] Inventor: Joseph J. McInerney, 260 Quarry Rd., Hummelstown, Pa. 17036

[21] Appl. No.: 674,913

[22] Filed: Mar. 26, 1991

[51] Int. Cl.⁵ .......................................... G01N 23/223
[52] U.S. Cl. ...................................... 378/44; 378/19; 378/87; 378/99
[58] Field of Search ............ 378/44, 49, 87, 62, 378/99, 42, 19, 21, 24, 25, 6, 5, 46, 90; 358/111

[56] References Cited

U.S. PATENT DOCUMENTS

| | | | |
|---|---|---|---|
| 2,670,401 | 2/1954 | Weinberg | 378/87 |
| 2,776,377 | 1/1957 | Anger | 250/363.02 |
| 3,497,691 | 2/1970 | Chen | 378/90 |
| 3,777,142 | 12/1973 | Grenier et al. | 250/363.02 |
| 3,819,256 | 4/1989 | Annis et al. | 378/87 |
| 3,927,318 | 12/1975 | Macovski | 250/272 |
| 4,101,774 | 7/1978 | Elzinga et al. | 250/402 |
| 4,229,651 | 10/1980 | Danos | 378/87 |
| 4,294,259 | 10/1981 | Picunko et al. | 250/363 |
| 4,480,332 | 10/1984 | Strecker | 378/6 |
| 4,495,636 | 1/1985 | Jacobs et al. | 378/87 |
| 4,799,247 | 1/1989 | Annis et al. | 378/87 |
| 4,809,312 | 2/1989 | Annis | 378/87 |
| 4,839,913 | 1/1989 | Annis et al. | 378/44 |
| 4,974,247 | 11/1990 | Friddell | 378/87 |
| 5,022,062 | 6/1991 | Annis et al. | 378/87 |

OTHER PUBLICATIONS

Clark et al., "The Use of Compton Scattered Gamma Rays for Tomography" May-Jun., 1976, pp. 225-235.
Towe et al., "X-ray Compton Imaging a High Speed Flying Spot X-ray Tube", Oct. 1981, pp. 712-721, vol. 28 (10).
Farmer et al., "A New Approach to Determination of Anatomical Cross Sections of the Body by Compton Scattering of Gamma-rays" Phys. Med. Biol., vol. 16, No. 4, pp. 577-586, 1971.
Guzzardi et al., "Recent Improvements in Compton Tomographic Imaging of the Lung and Possible Application to Object Recognition" IEEE Transaction on Nuclear Science vol. 34(3) pp. 667-671, Jun. 1987.
Lale P. G. "The Examination of Internal Tissues Using Gamma Ray Scatter with a Possible Extension to Mega Voltage Radiography" Phys. Med. Biol. vol. 4, pp. 159-167.
Palmer, et al., "Determination of Regional Myocardial Perfusion by X-ray Fluorescence" Investigative Radiology vol. 25 No. 5, pp. 486-494, May 1990.

*Primary Examiner*—Janice A. Howell
*Assistant Examiner*—Don Wong

[57] ABSTRACT

A narrow x-ray beam is scanned through the chest cavity of a subject to create a scattered radiation signal. The scattered radiation signal is used to construct a tomographic image of the contents of the subject's chest cavity on a display screen. A crosshair on the display screen is used to mark the location of a bypass graft in the image. A computer senses the position of the crosshair and subsequently positions a fluorescence detector over the subject to interrogate the location of the bypass graft within the chest cavity. A tracer material injected into the subject fluoresces as it passes through the irradiated bypass graft. The resulting fluorescence transient is recorded and provides a measure of graft patency and flow characteristics.

12 Claims, 5 Drawing Sheets

DEVICE FOR DETERMINING THE CHARACTERISTICS OF BLOOD FLOW THROUGH CORONARY BYPASS GRAFTS

BACKGROUND OF THE INVENTION

1. Field of the Invention

The present invention relates to an imaging and flow measuring device for evaluating patency and blood flow characteristics in coronary bypass grafts.

2. Prior Art

More than 70,000 coronary bypass graft operations are performed each year in the United States. Premature closure of these grafts is not rare, especially during the first post-operative year and sometimes occurs within a few hours of the bypass operation. When a bypass patient presents with chest pains that could indicate a blocked graft, the decision to reoperate on that patient is based upon an evaluation of blood flow through the patient's graft or grafts. The most common method for this evaluation is direct cineangiography. With this technique a catheter is passed via an artery to the ostium of the bypass graft. The tip of the catheter is inserted into the graft and a radiographic contrast agent is injected while an x-ray fluoroscopic image of the heart and graft vessel is being recorded. The patency of the graft is determined by whether or not the contrast agent is seen passing through the graft in the contrast enhanced image. This method, although effective requires hospitalization, minor surgery to gain access to an artery, exposes the patient to a substantial radiation dose, and because it transiently occludes the graft during injection of the contrast agent, carries some degree of morbidity and mortality. Although a number of safer alternative methods have been tried for evaluating the patency of bypass grafts, only two, cine-computed-tomography and magnetic resonance imaging (MRI) have achieved sufficient success to warrant serious consideration as alternatives to cineangiography.

With cine-computed-tomography, parallel tomographic image slices (usually 2 to 8 images) of the chest cavity are obtained simultaneously. Eight to ten sets of such images are obtained at approximately 50 millisecond intervals. With proper timing of these images, the relative timing of the passage of an intravenously injected radiographic contrast agent passing sequentially through the image slices can be obtained. Bypass graft patency and flow characteristics are determined from the appearance and timing of the contrast enhanced bright spots in the images.

With magnetic resonance imaging, two methods of graft evaluation have been employed. With spin-echo-MRI a single planar slice image through the chest cavity is obtained. With this technique a patent bypass graft will appear as a negative signal (i.e. a small dark spot in the image). With the alternative cine-MRI technique flow through a bypass graft will appear instead as a bright signal. Although the advantages of MRI techniques (x-ray exposures and radiographic contrast injections are not required) are significant, the MRI techniques do not achieve the accuracy of either cine-computed-tomography or cineangiography. Some of the difficulties with the MRI techniques include blood flow in normal vascular structures, hemostatic clips, mediastinal fibrosis or pericardial fluid, all of which can mimic the signal produced by a patent graft.

The cine-computed-tomography technique also has its limitations. Difficulties with graft patency and flow evaluations with this technique include false negatives (bright spots) due to surgical clips or calcified blood vessels or false positives (absence of bright spots) due to unusual bypass graft positions. Graft identification with cine-computed-tomography scans can also be made difficult by patient-to-patient variations in the timing of the arrival of the injected radiographic contrast agent. These scans are also expensive and require sufficient radiation exposure to preclude long term follow-up studies on individual patients. In addition, cine-computed-tomography requires, as does cineangiography, surgical access to a patient's arterial blood supply.

In spite of the significant progress with the MRI and cine-computed-tomography techniques, their limitations are such that hospitalization for cineangiography is still the method of choice in the vast majority of bypass graft evaluation studies. Most of the limitations with the MRI and cine-computed-tomography images relate to the association of graft identification with graft evaluation. If an isolated bright spot appears in the image it can be a patent graft, an artifact, or other structure. On the other hand if an isolated bright spot does not appear the bypass graft is not patent, not in the image plane, or hidden.

The present invention avoids many of the problems associated with other attempts to provide a safe effective evaluation of bypass graft patency. With this invention graft identification and graft evaluation are separate procedures. The location of a bypass graft within the chest cavity is determined, prior to a radiographic contrast injection, with a precise x-ray scatter profiling technique. Problems associated with timing the arrival of the radiographic contrast agent are avoided by continuously monitoring the bypass graft until the contrast agent makes its first pass through the heart. Continuous monitoring with the cine-computed-tomography or cineangiography techniques is not feasible because of substantial radiation exposure. Hardware for the present invention is less expensive than that required for the alternative techniques and the radiation dose per bypass graft evaluation is only 1/10 to 1/50 of that of cine-computed-tomography or cineangiography. The low radiation exposure of this invention makes it quite suitable for use as a screening device or for long-term follow-up studies of patient bypass graft patency. In addition, the application of the present invention eliminates the need for surgical access to the patient's arterial blood supply.

SUMMARY OF THE INVENTION

The principle object of this invention is to provide a device for use in evaluating the patency and flow characteristics of coronary bypass grafts that is safer and more accurate than alternative devices in use.

It is also an object of this invention to provide a device which is inexpensive relative to alternative devices for the same evaluations.

Another object is to provide this invention which in use will expose patients to less radiation than the most frequently used current devices for the same evaluation.

It is also an object of this invention to provide a graft evaluation method not sensitive to the patient-to-patient variations in the timing of arrival of blood flow tracers such as radiographic contrast agents.

A further object is to provide this invention which in use will not require inpatient hospitalization or surgical access to the patient's arterial blood supply.

An additional object of this invention is to provide a means for separating the identification and location of a coronary bypass graft from the evaluation of patency and flow characteristics in the said bypass graft.

Further objects of the said invention will become apparent from a consideration of the drawings and ensuing description thereof.

The foregoing objects can be accomplished by providing an imaging device that also includes a flow detection capability for evaluating the flow of a tracer dye through a bypass graft. In the preferred embodiment of the invention the imaging device consists of an x-ray source with a dual collimation system for producing a narrow beam of x-rays that rapidly sweep in a plane, a collimated scattered-radiation detector for detecting x-rays scattered from said plane to produce an image, a frame grabber for converting the said scattered-radiation detector's output signal from each source beam sweep to a scan line of an image, a motor and movable mounting assembly for scanning said scattered-radiation detector along the outward path of the source x-ray beam, thereby producing contiguous image scan lines, a monitor for displaying said image, and a fluorescence-radiation detector for evaluating graft patency and flow characteristics, and a computer for storing the said image, for controlling the said motor and movable mounting assembly, for image processing, and for producing and controlling the position of a crosshair image on the image display monitor. The said fluorescence-radiation detector comprises a collimated radiation detector tuned to detect fluorescence x-rays that result from the interaction between the said source beam of x-rays and a tracer injected into the patient's blood circulation. The collimator on the fluorescence-radiation detector is such that its field of view along the outgoing path of the said narrow source beam of source x-rays is approximately equal to the diameter of a typical human bypass graft. The output signals from the fluorescence-radiation detector are integrated and routed to a multichannel analyzer for display and subsequently to a computer for storage and/or data analysis. The observed timing and shape characteristics of the output signals from the fluorescence-radiation detector are used to evaluate the patency and flow characteristics of the bypass graft.

DESCRIPTION

Figure 1:
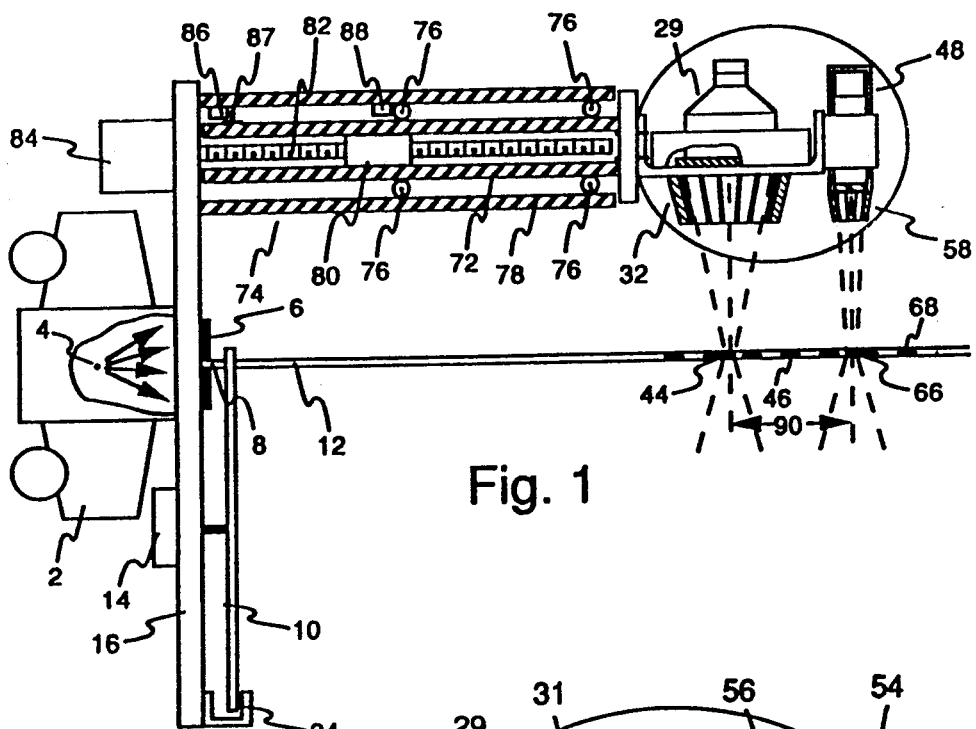
FIG. 1 is a side view in partial section of an imaging and flow detection device and x-ray source in accordance with the present invention.
Figure 1A:
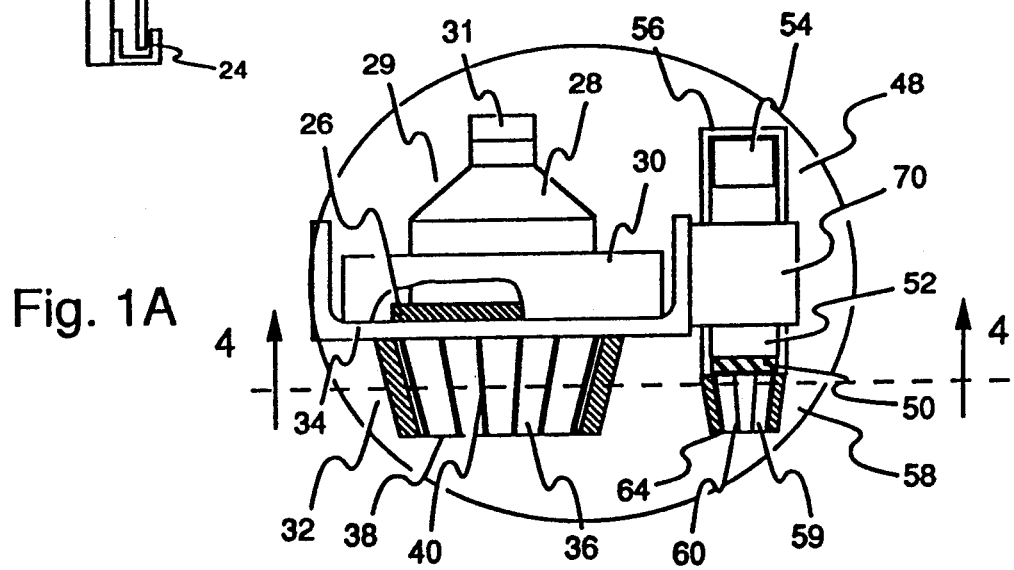
Figure 4:
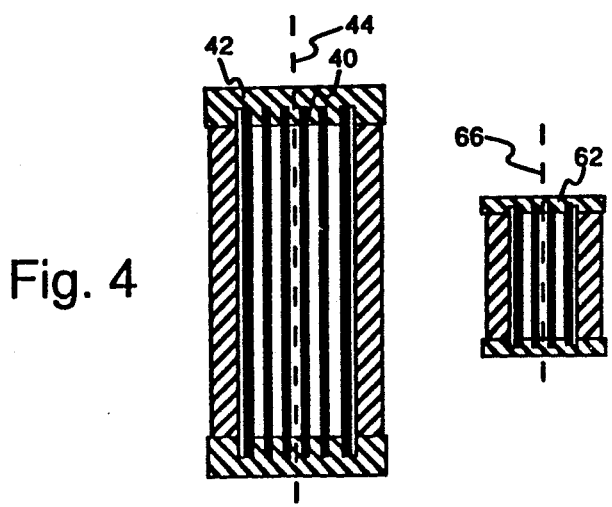
FIG. 4 is a partial cutaway view taken along line 4—4 of FIG. 1 and shows a sectional view of the scattered-radiation detector and fluorescence-radiation detector collimators.
Figure 3:
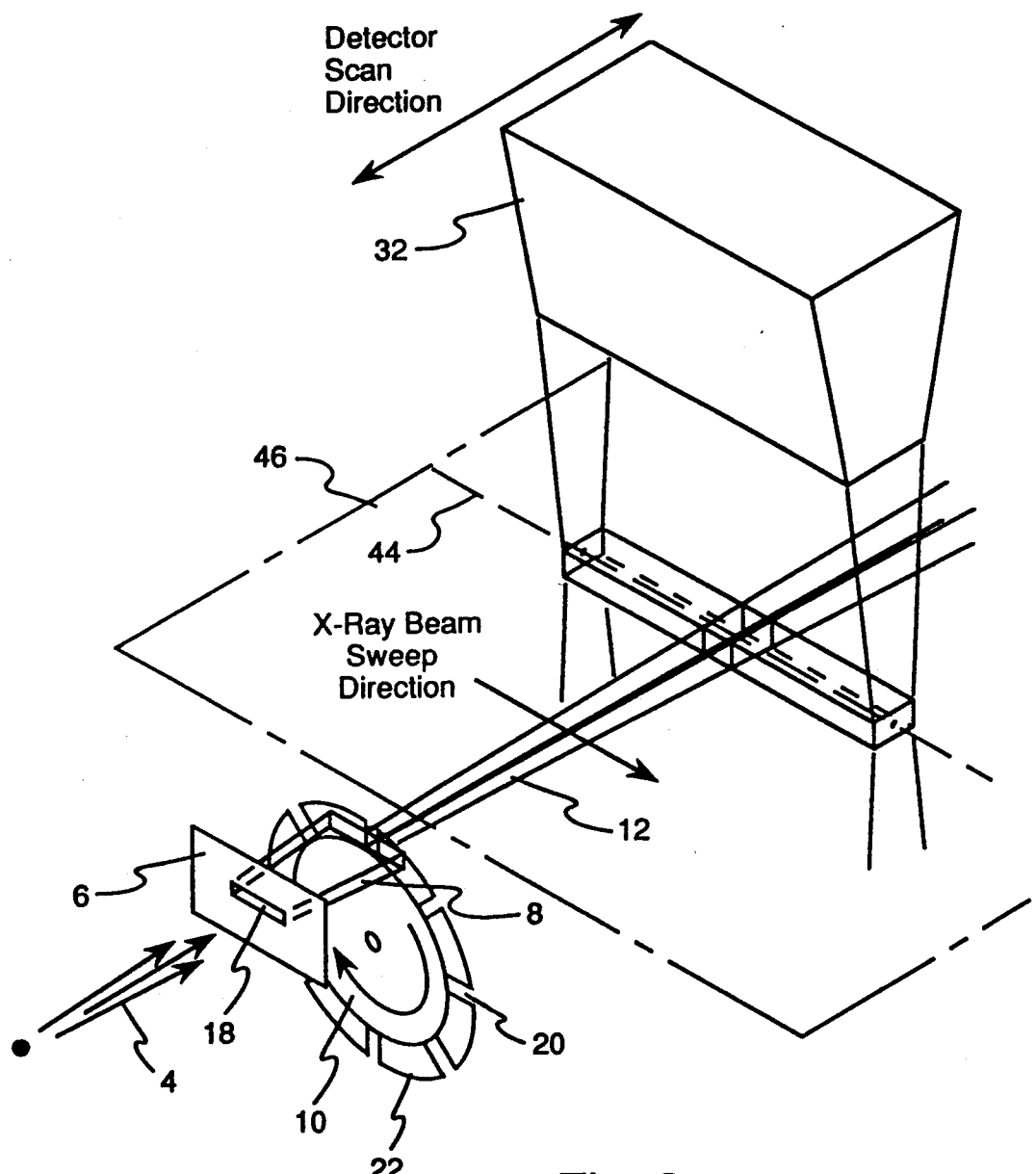
FIG. 3 is a schematic view from above of the dual collimation used to create a flying spot x-ray beam, and the field of view of the scattered-radiation detector.

Turning now to FIGS. 1 and 4, an x-ray source 2 produces an x-ray beam 4 which is collimated using a rectangular slot collimator 6 into a rectangular shaped x-ray beam 8. The said rectangular shaped x-ray beam 8 is further collimated by a rotating disc collimator 10 into a rectangular shaped sweeping x-ray beam 12. The x-ray source 2, rectangular collimator 6 and rotating disc collimator 10 with its motor 14 are mounted on a support plate 16. As shown in FIG. 3, the rectangular slot collimator 6 is a rectangular sheet of lead with a rectangular slot 18. The rotating disc collimator 10 consists of an aluminum disc with a plurality of uniformly spaced radial slots 20 and a lead strip 22 mounted between each pair of said slots. The disc collimator 10 is rotated with an AC synchronous motor 14 (FIG. 1) and is monitored with an infrared photo switch 24 that triggers and creates a sweep-start signal with the passage of each slot of the rotating disc collimator 10. Returning to FIGS. 1 and 4, the scattered-radiation detector 29 consists of a thallium-activated sodium iodide crystal 26 and photomultiplier tube (PMT) 28 sealed in a light tight housing 30, a connector 31 containing voltage divider circuitry for current mode operation of the PMT 28 output, a collimator assembly 32 and a support channel 34. The sodium iodide crystal 26 and photomultiplier 28 assembly is available from Harshaw/Filtrol Partnership of Solon, Ohio. The scattered-radiation detector collimator 32 includes a plurality of passageways 36 defined by lead collimator plates 40. The plates 40 are held in position by slotted end plates 42 and each passageway 36 is generally rectangular in cross section and is tapered substantially linearly from the end adjacent to the scattered-radiation detector support channel 34 to the collimator exit face 38. The passageways 36 are substantially straight and oriented such that planes defined by the centers of the said passageways approximately coincide along a line which defines the focal line 44 (See FIG. 3) of the collimator 32. Referring to FIGS. 1 and 3, a focal plane 46 is defined by a plane passing through the focal line 44 and normal to an average direction of the axes of the passageways 36.

Again referring to FIGS. 1 and 3, the scattered-radiation detector 29 and its collimator 32 are positioned such that the focal plane 46 of the collimator 32 coincides with the plane defined by the sweep of the x-ray beam 12.

Turning to FIGS. 1 and 4, the fluorescence-radiation detector 48 comprises a thallium-activated sodium iodide crystal 50, a photo multiplier tube 52, and a preamplifier 54 in a light tight housing 56. The fluorescence-radiation detector collimator assembly 58 is smaller but identical in its design to the scattered-radiation detector 29. The fluorescence-radiation detector collimator assembly includes a plurality of passageways 58 defined by collimator plates 60. The collimator plates 60 are held in place by slotted end plates 62. Each passageway 59 is generally rectangular in cross section and is tapered substantially linearly from the end adjacent to the thallium-activated sodium iodide crystal 50 to the exit face 64. The passageways are substantially straight and oriented such that the planes defined by the centers of the passageways approximately coincide along a line which defines the focal line 66 of the fluorescence-radiation detector collimator 58. A focal plane 68 of the fluorescence-radiation detector collimator 58 is defined by a plane passing through the focal line 66 and normal to an average direction of the axes of the passageways 58. The fluorescence-radiation detector 48 is positioned such that its collimator focal plane 68 coincides with the focal plane 46 of the scattered-radiation detector 29 and the plane defined by the sweep of the x-ray beam 12.

The fluorescence-radiation detector 48 is secured to the image detector support channel 34 with a bracket 70. The scattered-radiation detector support channel 34 is attached to the detector assembly support tube 72 which comprises the inner member of a telescoping detector support assembly 74. The detector assembly support tube 72 is supported by bearings 76 mounted on the detector support assembly outer tube 78. A detector assembly support tube drive head 80 is fixed to the detector assembly support tube 72 and engages the threads of a lead screw 82 so that rotation of the lead screw 82 in one direction or the other causes the detector assembly support tube 72 to advance in one direction or the other along the direction of the lead screw 82. The lead screw is connected to a stepping-motor 84. The stepping-motor 84 is electronically controlled and, in combination with the lead screw 82 permits the detector assembly support tube 72 and attached detectors 29, 48 to be positioned accurately along the directions of the lead screw. A stepping-motor under the trade name "Slo-Syn Stepper Motor" available from Velmex, Inc. of East Bloomfield, N.J. function suitably for this application. Limits for the translation of the detector assembly support tube 72 are set by a pair of translation limit switches 86 and 88. A first and second translation limit switch 86 and 88 are mounted on the detector support assembly outer tube 78 in positions such that they are contacted and depressed by the translation stop 87, mounted on the detector assembly support tube 72, when the detector assembly support tube reaches a first or second limit.

Figure 2:
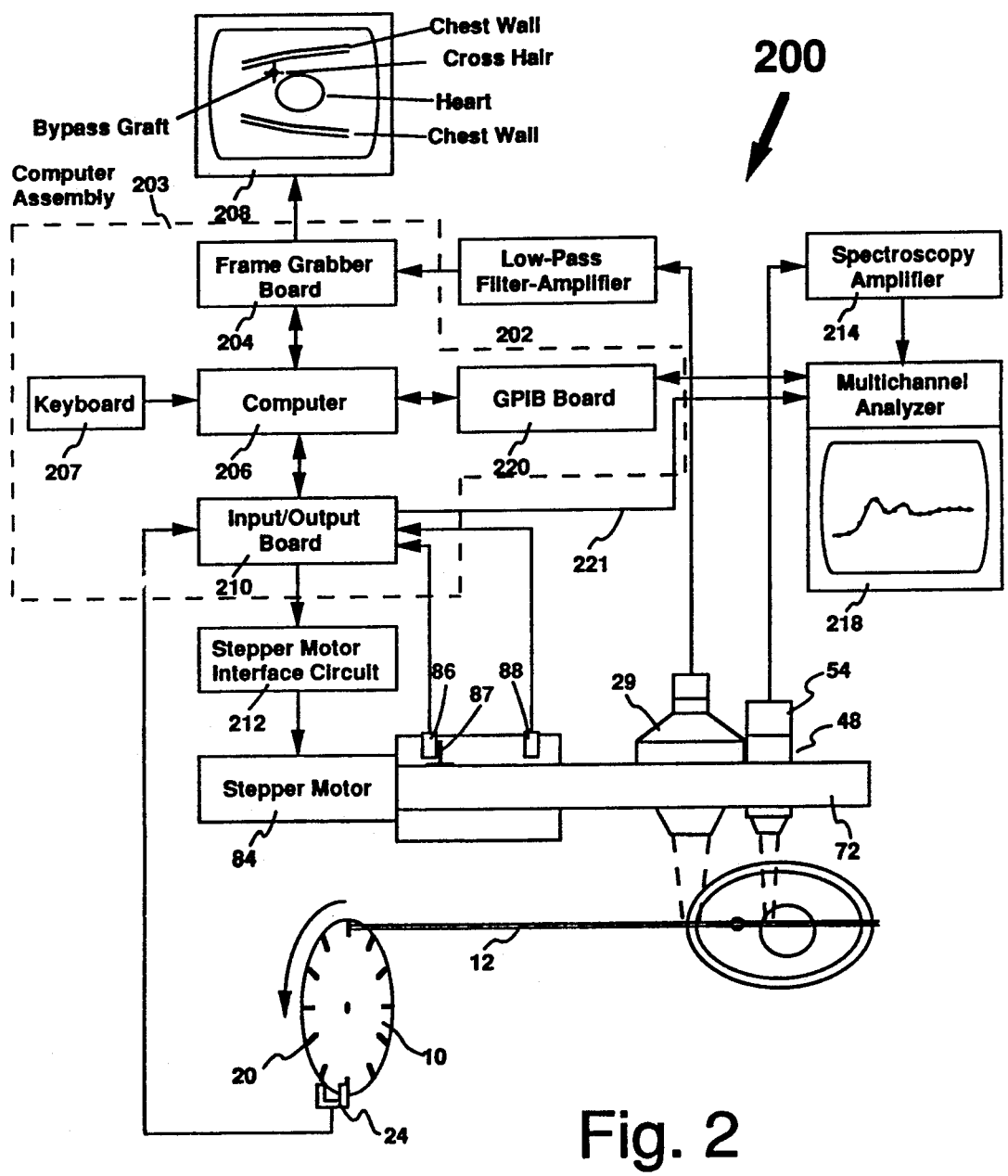
FIG. 2 is a block diagram of the present invention incorporating the preferred apparatus of FIG. 1.

Turning to FIG. 2, a block diagram 200 of a preferred configuration of the present invention is shown. For simplicity, the x-ray source 2, rectangular slot collimator 6, support plate 16, and details of the telescoping support assembly 74 are not shown. The radiation intensity signal from the scattered-radiation detector 29 is connected to the input of a low-pass filter/amplifier 202. The output of the low-pass amplifier 202 is connected in turn to the input of an image display interface means. For the purposes of this invention that means consists of a frame-grabber board 204 installed as part of the computer assembly 203. The computer assembly 203 comprises a computer 206, a keyboard 207, a frame grabber board 204, an input/output board 210, and a general purpose interface board (GPIB) 220. The output from the frame-grabber board 204 is in turn connected to an input of an image display monitor 208. The sweep-start signal output of the infrared photo switch 24 is connected to the computer assembly 203 input-/output board 210 installed in the computer 206. A position control signal input means is provided with a stepping-motor interface circuit 212 connected to one of the outputs of the input/output board 210 and to the stepping-motor 84. The stepping-motor interface circuit 212 translates a digital command by the computer 206, directed to the stepping-motor to rotate clockwise or counterclockwise one step, into a motor drive signal transmitted to the stepping-motor to cause the motor to rotate one step in the direction specified. The computer 206 can therefore control the rotation of the stepping-motor one step at a time to rotate the lead screw 82 (FIG. 1) in either direction thereby translating the detector assembly support tube 72 in either direction along the path of the x-ray beam 12. The outputs from the first and second translation limit switches 86 and 88 are connected to input ports on the said input/output board 210. The computer 206 includes the following components: a central processing unit (CPU), a read-only memory (ROM), a random access memory (RAM) and interface circuits for a keyboard, a CRT display, a hard disk drive for mass data storage, and interface slots for installing accessory boards such as the frame grabber 204, GPIB 220, and input/output 210 boards. A suitable computer is available under the trade name "Performer 16" from Ironics, Inc. of Ithaca, N.Y. A suitable input/output board 210 is available under the model number DT-1401 from Data Translation of Marlboro, Mass. A frame grabber board 204 suitable for the purposes of this invention is available under the model number DT-1451 from Data Translation of Marlboro, Mass. A stepping-motor interface circuit 212 suitable for the purposes of this invention is available under the model number 3180-PTO from Superior Electric of Bristol, Conn. An image display monitor suitable for the purpose of this invention is available under the model number FA3425 from Mitsubishi Electronics America, Inc. of Torrance, Calif. The output of the fluorescence-radiation detector preamplifier 54 is connected to the input of a pulse shaping spectroscopy amplifier 214. The output of the pulse shaping spectroscopy amplifier 214 is connected to an energy spectrum analysis means. Specifically, the pulse shaping spectroscopy amplifier 214 is connected to the input of a multichannel analyser 218. A spectrum analysis control interface 221 between the input/output board 210 and the multichannel analyzer 218 permits computer 206 control of data acquisition by the multichannel analyser 218. A pulse shaping spectroscopy amplifier (model 673), and multichannel analyser (model 7150) suitable for the applications of this invention are available from EG & G ORTEC of Oak Ridge, Tenn. The output of the multichannel analyser 218 is connected to the computer 206 via a General Purpose Interface Board (GPIB) 220. A GPIB board suitable for the application of this invention is model number IV-1621 from Ironics, Inc. of Ithaca, N.Y.

OPERATION

A preferred method for operating the imaging/flow detecting system discussed above to collect data for constructing a tomographic image of a cross-sectional area of the chest in the body of a subject will now be described. A preliminary fluoroscopic examination of the chest of the subject may be carried out if necessary to locate the lung cavity and the approximate position of the heart within the lung cavity. Turning to FIGS. 1 and 2, the is positioned supine in front of the x-ray beam source 2 with the scattered-radiation detector assembly 29 located generally above the area of the heart within the chest. The scattered-radiation detector assembly 29 is placed in a pre-imaging position by the computer 206. Specifically, the detector assembly support tube 72 is translated toward the first limit switch 86. The computer 206 monitors the first limit switch 86 via the input-/output board 210 and stops translation of the detector assembly support tube 72 when the translation stop 87 trips the first translation limit switch 86. The subject is located such that the focal line 44 of the scattered-radiation detector 29 falls just outside the chest of the subject.

Figure 5:
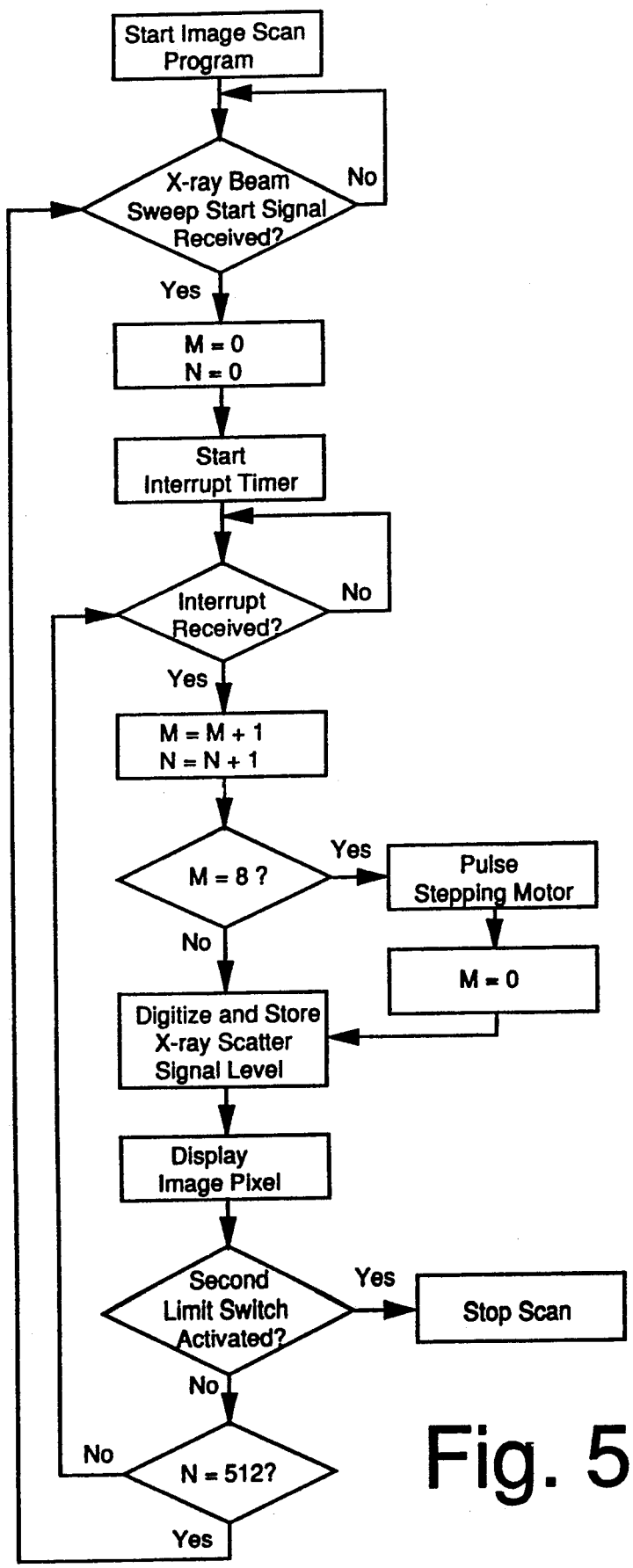
FIG. 5 is a flow diagram of a preferred imaging procedure carried out by the preferred imaging system of FIG. 2.

A flow diagram of a preferred imaging is shown in FIG. 5. Continuing also with FIGS. 1 and 2, the x-ray source 2 is turned on and a sweeping x-ray beam 12 is directed into the chest of the subject. The location of the infrared photo switch 24 is such that it triggers and sends a sweep-start signal to the computer 206 via the input/output board 210 as each of the slots 20 on the rotating disc collimator 10 begins a sweep of the collimated x-ray beam 12. In the preferred embodiment of this invention, the computer 206 starts an internal timing circuit which interrupts the computer 206 five hundred and twelve times during each sweep of the x-ray beam 12. During each sweep, the output signal from the scattered-radiation detector 29 is processed by the low-pass filter/amplifier 202 and presented to the input of the frame grabber board 204. At each timing circuit interrupt, the computer 206 instructs the frame grabber board 204 to digitize and store the current input signal level from the low-pass filter/amplifier 202 in the frame grabber board 204 resident image memory. Starting with the frame grabber board 204 first image memory location, five hundred and twelve consecutive memory locations correspond, on a one-to-one basis, to the five hundred and twelve image pixels that the frame grabber board will send for display as the first raster line on the image display monitor 208. The intensity of each image pixel, corresponding to the digitized value of the input signal level from the low-pass filter/amplifier 202 input to the frame grabber 204, is displayed on the image monitor 208 as it is received. Contiguous blocks of five hundred and twelve image memory locations on the frame grabber board 204 correspond to contiguous raster lines that the frame grabber board 204 will send to the display monitor 208. These contiguous image raster lines are acquired by scanning the scattered-radiation detector 29 along the lead screw of the axis. As noted above, the computer is interrupted five hundred and twelve times on each sweep of the x-ray beam 12. On every eighth interrupt the computer 206 directs the stepping-motor 84 to advance the detector assembly support tube 72 one step in the direction from the said pre-imaging position towards the second limit switch 88 position. At the completion of the five hundred and twelve interrupts during a single sweep of the x-ray beam 12, the computer awaits the next signal from the infrared photo switch 24 and upon receipt of said signal repeats the above procedure to display the succeeding raster image line on the image display monitor 208. As the detector assembly support tube 72 is advanced and image raster lines are displayed in this manner, the computer 206 maintains a motor step count in its memory. This count is cleared to zero at the said pre-imaging position. For each step of the stepping-motor 84 driving the detector assembly support tube 72 towards the second limit switch 88 position, the motor step count is incremented by one. As a result, the motor step count equals the number of steps the stepping-motor has driven the scattered-radiation detector 29 from the said pre-imaging position.

The above imaging procedure continues until the computer 206 receives a signal from the second limit switch 88 indicating that the imaging scan is completed. Approximately four hundred and eighty contiguous raster lines of a tomographic image of a slice of the subject's chest, corresponding to the sweep path of the x-ray beam 12, will be displayed on the image monitor 208. In addition, the image is now stored in a sequential array in memory on the frame grabber board 204 in such a manner that each image pixel can be associated with a particular motor step count and a specific number of computer 206 interrupts from the start of the said image raster line containing that pixel. Specifically, each image pixel on the image display monitor 208 has a one-to-one correspondence with a memory location on the frame grabber board 204. Starting with the first image pixel memory location, every eighth memory location corresponds to an increment in the stepping-motor 84 step count, and each contiguous set of five hundred and twelve frame grabber board 204 memory locations corresponds to one image raster line. The location of each pixel on an image raster line corresponds to the number of computer interrupts given to generate the said image pixel on that raster line.

At the completion of image acquisition the x-ray source 2 is turned off and the computer begins to step the stepping-motor 84 in such a direction as to translate the detector assembly support tube 72 from the second limit switch 88 position toward the first limit switch 86 position. The computer 206 continues to step the stepping-motor 84 in this manner until a signal from the first limit switch 86 indicates that the detector assembly support tube 72 has returned to the preimaging position.

Figure 6:
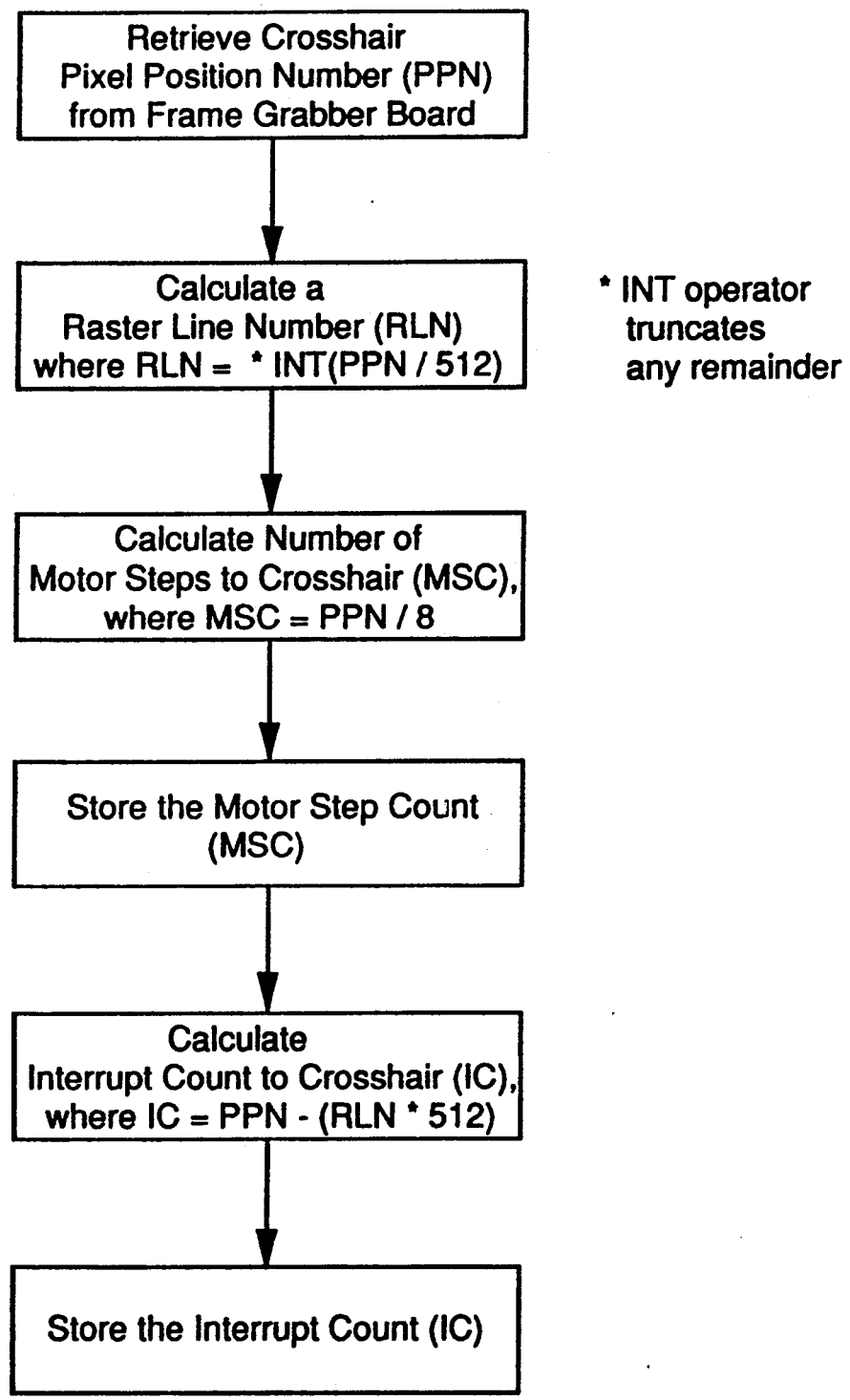
FIG. 6 is a flow diagram of a calculation procedure for locating the position of a bypass graft relative to the configuration of the imaging device shown in FIG. 1.

In addition to displaying the acquired image, the frame grabber board 204 continuously displays a crosshair on the image display monitor 208. The crosshair can be moved from pixel-to-pixel on the image screen using the arrow keys on the computer keyboard 207. The location of the crosshair on the image display monitor 208 is in a one-to-one correspondence with the image pixel data stored in the frame grabber board memory. In particular, the crosshair image pixel positions are numbered sequentially, starting with one, at the first image pixel on the first image raster line. The location of the crosshair relative to the image memory is stored in a location that can be read by the computer 206. With this information, the computer 206 calculates how many stepping-motor 84 steps would be required to return the scattered-radiation detector 29 to the location where data for the image pixel at the crosshair was acquired. In addition, the computer 206 calculates which of the five hundred and twelve interrupts on the same pixel's raster line was used to trigger the frame grabber board 204 to acquire data and to display that particular pixel. A preferred method for these calculations is shown in FIG. 6.

Continuing with FIGS. 1 and 2, the arrow keys on the computer 206 key board are next used to position the display monitor 208 crosshair at the position of a detected bypass graft. The bypass graft will appear as an isolated spot or alternatively as an irregularity on the otherwise relatively smooth surface of the subject's heart. With the crosshair thus positioned approximately at the center of the bypass graft, the computer 206 is instructed to use the location of the crosshair to compute the number of steps required by the stepping-motor 84 to position the scattered-radiation detector 29 at the location it had when that image pixel data was acquired. The said number of steps is then reduced by a sufficient number of steps to account for the distance 90 separating the scattered-radiation detector and fluorescence-radiation detector focal lines 44, and 66. The step reduction can be calculated from the distance 90 between the scattered-radiation detector 29 and fluorescence-radiation detector 48 focal lines and the translation distance for a single step of the stepping-motor 84. The latter distance is known from the angle per step of the said stepping-motor and the pitch of the lead screw 82. The reduced number of steps then represents the number of steps that the detector assembly support tube 72 must be driven to position the fluorescence-radiation detector 48 rather than the scattered-radiation detector 29 at the location of the bypass graft. In the preferred embodiment of the invention, the fluorescence-radiation detector 48 is positioned further from the x-ray source 2 than the scattered-radiation detector 29. The fluorescence-radiation detector 48 could alternatively have been placed closer to the x-ray source 2 than the scattered-radiation detector 29. In that case, the computed number of steps required to cover the distance 90 between the scattered-radiation detector and fluorescence-radiation detector focal lines would be added to instead of subtracted from the calculated number of steps required to return the scattered-radiation detector to the crosshair position.

After calculating the step count required for positioning the fluorescence-radiation detector 48 at the pixel position associated with the bypass graft, the computer advances the detector assembly support tube 72 that number of steps. Next, the x-ray source 2 is turned on and the sweeping x-ray beam 12 is again directed into the chest of the subject. The infrared photo switch 24 is triggered at the start of each x-ray beam sweep to send a sweep-start signal to the Computer 206 to start an internal timing circuit which generates an interrupt signal five hundred and twelve times during each sweep of the x-ray beam 12. A tracer solution is next injected into a vein of the subject over a period of five to ten seconds. A suitable tracer for this purpose is the commonly used iodine based radiographic contrast agent sold under the trade name "Omnipaque 350" manufactured by Winthrop Pharmaceuticals of Sterling Drug, Inc. of New York. Although other traces are also suitable, iodine based tracers are used in the preferred embodiment of this invention. As the tracer solution passes through the patient's bypass graft it will be stimulated by the sweeping x-ray beam 12 to emit iodine fluorescence x-rays. During each sweep of the x-ray beam 12, the output signal from the fluorescence-radiation detector photomultiplier tube 52 is processed by the fluorescence-radiation detector preamplifier 54, which in turn presents the processed output signal pulses to the spectroscopy amplifier 214. The spectroscopy amplifier further amplifies and shapes the output signal pulses for presentation to the input of the multichannel analyser 218. Upper and lower level discriminators on the multichannel analyser are set to accept only those input signal pulses from the spectroscopy amplifier 214 that fall within a narrow energy band corresponding to the primary characteristic radiation of iodine. The multichannel analyser 218 is also configured to acquire data in a multiscaling mode. In this mode, input signal pulses are counted for a pre-programmed time interval and the cumulative count level for that interval is displayed in a channel on the multichannel analyser 218 display screen. At the expiration of the said pre-programmed time interval, the multichannel analyser 218 resets its count to zero and proceeds to count input pulses for display in the succeeding channel. For the present embodiment of the invention, a programmed time interval of one second per channel is preferred. Generally twenty to forty channels of data are acquired.

It is preferred to measure a bypass graft flow transient by accepting signal output from the fluorescence-radiation detector 48 only during the time when the sweeping x-ray beam 12 is irradiating the position of the bypass graft. A spectrum analysis control interface input 221 to the multichannel analyser 218 from the input/output board 210 transmits a voltage signal to the multichannel analyser 218 from the computer 206 that, in its "on" state of approximately plus five volts, will signal the multichannel analyser to stop counting the input signal pulses from the fluorescence-radiation detector 48. The position of the bypass graft along the sweep of the x-ray beam 12 is known to the computer from the crosshair location stored in the memory of the frame grabber board 204. The computer 206 controls the processing and counting of input signal pulses in the multichannel analyser 218 by using the spectrum analysis control interface input 221. The said input 221 is maintained at approximately plus five volts during the sweep of the x-ray beam 12 except for the time interval encompassed by approximately ten interrupts before and after the interrupt corresponding to the position of the image display monitor crosshair. An interrupt count, corresponding to the position of the display monitor 208 crosshair, is calculated as shown in FIG. 6. Only those signal pulses which arrive at the multichannel analyser 218 during the time interval when the sweeping x-ray beam 12 is close to, or in contact with, the bypass graft are counted. As each channel of data on the multichannel analyser 218 is acquired, it is displayed on the multichannel analyser 218 display screen. The data displayed on the multichannel analyser 218 is also stored in multichannel analyser 218 memory. This data is acquired by the computer 206 for storage via the GPIB board 220.

It is not intended to limit the present invention to the specific embodiments described above. For example, the sweeping x-ray beam 12 can be created using an x-ray tube with an electronically controlled sweeping focal spot and a stationary single hole collimator. Tracers other than the iodine based radiographic contrast agent used in the specific embodiment of this invention can also be used. Any tracer containing amounts of relatively high atomic number material which will fluoresce when excited by the x-ray beam 12 and emit its characteristic radiation would be suitable. The material should have a relatively high atomic number so that the fluorescence emission will be sufficiently high energy to escape the subject examined without excessive attenuation. In the present embodiment of the invention, sodium iodide based detectors were used. Many other types of radiation detectors, such as those that are lithium or germanium based, are suitable for the purposes of this invention. Further, it is not necessary to evaluate the patency and flow characteristics of the bypass graft with the sweeping x-ray beam 12. A stationary beam aimed at the known location of the bypass graft would suffice and eliminate the need for the coincidence input 221. In addition, separate detectors for flow and imaging are not required. It is recognized that a single detector configured for pulse height analysis could be used for imaging also by processing its signals through a count-rate meter prior to presentation to the frame grabber board 204 of the present embodiment. It is recognized that these and other changes may be made in the apparatus and process specifically described herein without departing from the scope and teachings of the invention. It is contemplated that the appended claims will cover any such modifications as fall within the true spirit and scope of the invention.

What is claimed is:

1. An apparatus for monitoring flow through a coronary bypass graft in a subject comprising:
   (a) x-ray source means for generating a shaped x-ray beam for directing into the chest cavity of the subject to scatter from and fluoresce the contents of said chest cavity;
   (b) means for sweeping the said shaped x-ray beam so that a plurality of locations comprising a cross-section of the chest of said subject will emit scattered and fluorescence radiation;
   (c) a means for creating a sweep-start signal at the start of each sweep of the sweeping x-ray beam;
   (d) scattered- and fluorescence-radiation detector means for detection, at a plurality of locations, the scatter and fluorescence radiation emitted from the chest cavity of said subject, said detection assembly means including:
      (d.1) a scattered-radiation detector, said scattered-radiation detector having a directional radiation receptance port and a radiation-intensity signal output and being adapted to produce a radiation intensity signal at said output which is a measure of the intensity of radiation incident upon the scattered-radiation detector radiation receptance port and propagating in a direction admitted by the scattered-radiation detector radiation receptance port having a limited field of view;
      (d.2) a fluorescence-radiation detector, said fluorescence-radiation detector having a directional radiation receptance port and a radiation-intensity signal output and being adapted to produce a radiation-intensity signal at said output which is a measure of the intensity of radiation incident upon the fluorescence-radiation detector radiation receptance port and propagating in a direction admitted by the fluorescence-radiation detector radiation receptance port having a limited field of view;
      (d.3) a means for positioning of the scattered-radiation detector at a plurality of locations;
      (d.4) a means for positioning of the fluorescence-radiation detector at a plurality of locations;
   (e) position control signal input means to control the positions of the said scattered- and fluorescence-radiation detectors;
   (f) an x-ray energy spectrum analysis means for isolating a selected energy level of fluorescence radiation;
   (g) a means for displaying and recording the intensity of said selected fluorescence-radiation as it changes with time;
   (h) a computer assembly comprising:
      (h.1) an image display interface means for creating a cross-sectional image of the chest of the subject from the scattered-radiation signal output from the scattered-radiation detector;
      (h.2) an input/output means;
   (i) an image display means for displaying said cross sectional image of the chest of the subject.

2. Apparatus as recited in claim 1 wherein the said computer assembly input/output means includes an input which senses the said sweep-start signal.

3. Apparatus as cited in claim 1 wherein the said input-output means includes an interface with the said position control signal input means.

4. Apparatus as cited in claim 1 wherein the said input/output means includes a spectrum analysis control interface with said x-ray energy spectrum analysis means to control the processing of signals input to the energy spectrum analysis means.

5. Apparatus as recited in claim 1 wherein the said image display interface means includes a means for encoding the said cross sectional image in computer memory in such a manner as to relate each image pixel to an ordered memory location.

6. Apparatus as recited in claim 5 wherein the said means for encoding the cross-sectional image encodes:
   (a) the position of the scattered-radiation detector at the time each image pixel was acquired;
   (b) the configuration of the means for sweeping the shaped x-ray beam at the time each image pixel was acquired.

7. Apparatus as recited in claim 1 wherein the image display interface means for displaying the cross-sectional image includes a means selecting an individual pixel on the said image.

8. Apparatus as recited in claim 7 wherein means for selecting an individual image pixel includes:
   (a) a means to relate the position of the said individual image pixel to the position of the scattered-radiation detector at the time the data for that image pixel was acquired;
   (b) a means to relate the position of the said individual image pixel to the configuration of the means for sweeping the shaped x-ray beam at the time the data for the said image pixel was acquired.

9. Apparatus as recited in claim 1 wherein the said computer assembly can direct the position control signal input means to position the fluorescence-radiation detector such that the fluorescence-radiation detector is approximately centered at the position held by the scattered-radiation detector when the scattered-radiation detector acquired data for a selected image pixel.

10. Apparatus as recited in claim 4 wherein the said spectrum analysis control interface means restricts spectrum analysis means data collection to the approximate time interval during which the sweeping x-ray beam is passing through the chest of the subject at the location corresponding to a selected image pixel.

11. Apparatus as recited in claim 1 wherein the energy spectrum analysis means includes a means for storing the data it acquires.

12. Apparatus as recited in claim 11 wherein the said energy spectrum analysis means includes a means for transmitting stored data to a computer.

* * * * *

UNITED STATES PATENT AND TRADEMARK OFFICE
CERTIFICATE OF CORRECTION

PATENT NO. : 5,105,452

DATED : April 14, 1992

INVENTOR(S) : Joseph J. McInerney,

It is certified that error appears in the above-identified patent and that said Letters Patent is hereby corrected as shown below:

Column 1, line 7, insert the clause - This invention was made with government support under Public Health Service Grant number R01 HL40934 awarded by the National Institutes of Health. The government has certain rights in the invention.

Column 6, line 57, after "and 2, the" insert - subject -

Signed and Sealed this

Twenty-fourth Day of August, 1993

Attest:

BRUCE LEHMAN

*Attesting Officer*  *Commissioner of Patents and Trademarks*